US012708768B2

(12) United States Patent
Truckai et al.

(10) Patent No.: US 12,708,768 B2
(45) Date of Patent: Aug. 18, 2026

(54) MEDICAL DEVICE AND METHOD OF USE

(71) Applicant: Meditrina, Inc., San Jose, CA (US)

(72) Inventors: Csaba Truckai, Saratoga, CA (US); Akos Toth, Cupertino, CA (US); John H. Shadduck, Menlo Park, CA (US)

(73) Assignee: Meditrina, Inc., San Jose, CA (US)

( * ) Notice: Subject to any disclaimer, the term of this patent is extended or adjusted under 35 U.S.C. 154(b) by 0 days.

(21) Appl. No.: 19/353,253

(22) Filed: Oct. 8, 2025

(65) Prior Publication Data

US 2026/0097205 A1 Apr. 9, 2026

Related U.S. Application Data

(60) Provisional application No. 63/750,420, filed on Jan. 28, 2025, provisional application No. 63/705,481, filed on Oct. 9, 2024.

(51) Int. Cl.

*A61N 1/36* (2006.01)
*A61M 1/00* (2006.01)
*A61N 1/05* (2006.01)
*A61N 1/08* (2006.01)

(52) U.S. Cl.

CPC ........... *A61N 1/36007* (2013.01); *A61M 1/77* (2021.05); *A61M 1/87* (2021.05); *A61N 1/0524* (2013.01); *A61N 1/08* (2013.01); *A61M 2202/0413* (2013.01); *A61M 2205/054* (2013.01); *A61M 2205/3344* (2013.01); *A61M 2205/8206* (2013.01); *A61M 2210/1433* (2013.01)

(58) Field of Classification Search

None

See application file for complete search history.

(56) References Cited

U.S. PATENT DOCUMENTS

| | | | | |
|---|---|---|---|---|
| 5,129,813 | A | 7/1992 | Shepherd | |
| 9,572,972 | B2 * | 2/2017 | Garfield | A61M 25/10 |
| 2012/0109233 | A1 | 5/2012 | Lee et al. | |
| 2013/0261702 | A1 | 10/2013 | Garfield et al. | |
| 2014/0378756 | A1 | 12/2014 | Buster et al. | |
| 2016/0228179 | A1 | 8/2016 | Truckai | |
| 2021/0361311 | A1 * | 11/2021 | Truckai | A61B 17/32002 |
| 2021/0369555 | A1 * | 12/2021 | Truckai | A61H 23/008 |
| 2022/0175420 | A1 | 6/2022 | Norred et al. | |
| 2023/0136199 | A1 * | 5/2023 | Shadduck | A61M 25/1011 604/500 |

OTHER PUBLICATIONS

Kim et al. “Polyacrylamide-treated kaolin: A fabric study,” *Applied Clay Science*, 45:4, pp. 270-279, Jun. 12, 2009.

Yang et al. “Effect of surface modified kaolin on properties of polypropylene grafted maleic anhydride,” *Results in Physics*, vol. 7, pp. 969-974, Feb. 22, 2017.

* cited by examiner

*Primary Examiner* — Carl H Layno
*Assistant Examiner* — Bryan Mcallister Lee
(74) *Attorney, Agent, or Firm* — Levine Bagade Han LLP

(57) ABSTRACT

Devices and methods for treating postpartum hemorrhaging, including devices and methods for trans-cervical introduction into a uterine cavity of a patient comprising an elongated shaft with an expandable working end; a negative pressure source coupled to an extraction lumen in the elongated shaft; an electrode arrangement carried by the expandable working end; and an electrical source and controller coupled to the electrode arrangement adapted to deliver electrical stimulation to walls of the uterine cavity.

21 Claims, 14 Drawing Sheets

MEDICAL DEVICE AND METHOD OF USE

FIELD OF THE INVENTION

The application is a non-provisional application of U.S. Provisional application No. 63/705,481 filed Oct. 9, 2024, and 63/750,420 filed Jan. 28, 2025. The entirety of both of which is incorporated by reference.

FIELD OF THE INVENTION

This disclosure relates generally to the field of gynecology and, more specifically, to devices for treating postpartum hemorrhaging.

FIELD OF THE INVENTION

This disclosure relates generally to the field of gynecology and, more specifically, to devices for treating postpartum hemorrhaging.

BACKGROUND

Postpartum hemorrhage, defined as excessive blood loss after birth, is a significant source of maternal morbidity and is the leading cause of maternal death worldwide. Inability to control postpartum bleeding can result in myocardial ischemia, multiple blood transfusions, in severe cases, a hysterectomy, and death. The cause of postpartum hemorrhage, in approximately 80% of cases, is uterine atony. Uterine atony is a loss of tone in the uterine musculature postpartum, resulting in the failure of uterine muscles to contract tonically and stop postpartum bleeding. Normally, contraction of the uterine muscle compresses the vessels and reduces blood flow after delivery. This increases coagulation, which prevents bleeding. However, a lack of uterine muscle contractions can cause an acute postpartum hemorrhage.

SUMMARY OF THE INVENTION

A variation of the present invention provides a trans-cervical treatment device that is deployed in a patient's uterine cavity to provide negative pressure and contemporaneous electrical stimulation to uterine muscles to cause the uterine walls to contract. The treatment device carries an electrode arrangement comprising a plurality of electrodes on an outer surface of an expanded working end that electrically stimulates muscles to treat uterine atony. The negative pressure provides a mechanical stimulus to the walls of the postpartum uterus, also facilitating contractile movements in muscles in the uterine walls.

Variations of the present disclosure include methods for treating uterine atony to mitigate postpartum hemorrhaging in a patient. For example, such a method can include: positioning an electrode arrangement within a uterine cavity, wherein the electrode arrangement includes a plurality of electrodes disposed on an outward-facing surface of a working end that is configured to be expandable; creating a seal near an entrance to the uterine cavity; applying negative pressure through the working end to contract the uterine cavity and draw a uterine wall into contact with the electrode arrangement; and delivering electrical stimulation current to the uterine wall from the electrode arrangement to cause contraction of uterine muscles and to reduce postpartum bleeding.

In methods and systems of the present disclosure, the working end can be configured to expand in a planar configuration.

Positioning the electrode arrangement can include introducing the working end into the uterine cavity through a birth canal of the patient.

Variations of the present disclosure can include methods wherein positioning the electrode arrangement includes the working end expanding from a linear contracted shape for introduction to an expanded planar shape.

Variations of the present disclosure can include methods wherein the linear contracted shape is a tensioned state of the working end, and the expanded planar shape is a repose state of the working end.

The methods and systems described herein can include introducing a lavage fluid from the working end into the uterine cavity. Additionally, the methods and systems can optionally include extracting at least one of blood and irrigation fluid from the uterine cavity with the negative pressure.

Variations of the present disclosure can include methods, wherein delivering electrical stimulation current includes maintaining electrical stimulation current for at least 1 minute, at least 5 minutes, or at least 10 minutes.

Variations of the present disclosure can include methods, wherein applying negative pressure includes maintaining negative pressure for at least 10 minutes.

Variations of the present disclosure can include methods, wherein the electrical stimulation current is delivered by an electrical source and controller that generates an output current between 0.01 milliamperes and 40.00 milliamperes.

The methods and systems described herein can use a battery or other portable power source as the electrical source.

Variations of the present disclosure can include methods, wherein the electrical stimulation current is delivered with a pulse width that ranges from about 0.1 milliseconds to 1 second.

Variations of the present disclosure can include methods, wherein the electrical stimulation current has pulse train durations from 1 second to 1 minute.

Variations of the present disclosure can include methods, wherein the electrical stimulation current is delivered from 0.1 Hz to 50 Hz. Variations of the present disclosure can include methods, wherein the negative pressure is from 50 mm Hg to 90 mm Hg.

Variations of the present disclosure can include systems for treating postpartum hemorrhaging in a patient. For example, such a system can include a device configured for trans-cervical introduction into a uterine cavity of a patient including an elongated shaft with an expandable working end; a negative pressure source coupled to an extraction lumen in the elongated shaft; an electrode arrangement carried by the expandable working end; and an electrical source and controller coupled to the electrode arrangement adapted to deliver electrical stimulation to walls of the uterine cavity.

Variations of the present disclosure can include a system, further including an expandable seal carried on the elongated shaft.

Variations of the present disclosure can include a system wherein the expandable seal includes a balloon.

Variations of the present disclosure can include a system wherein the expandable working end is expanded by at least one resilient metal member.

Variations of the present disclosure can include a system wherein the electrode arrangement is disposed on a peripheral surface of the expandable working end.

Variations of the present disclosure can include a system, wherein the electrode arrangement is disposed on an inferior surface and a superior surface of the expandable working end.

DETAILED DESCRIPTION

The present disclosure describes variations of a system for causing uterine contraction to aid in contracting a patient's uterus following childbirth in order to minimize or prevent postpartum hemorrhaging. Some variations described herein are utilized to collapse a patient's uterus toward an anatomically normal postpartum state. Additional variations described herein provide negative pressure within the uterus contemporaneous with electrical stimulation to cause muscle contraction to reduce postpartum bleeding.

Figure 1:
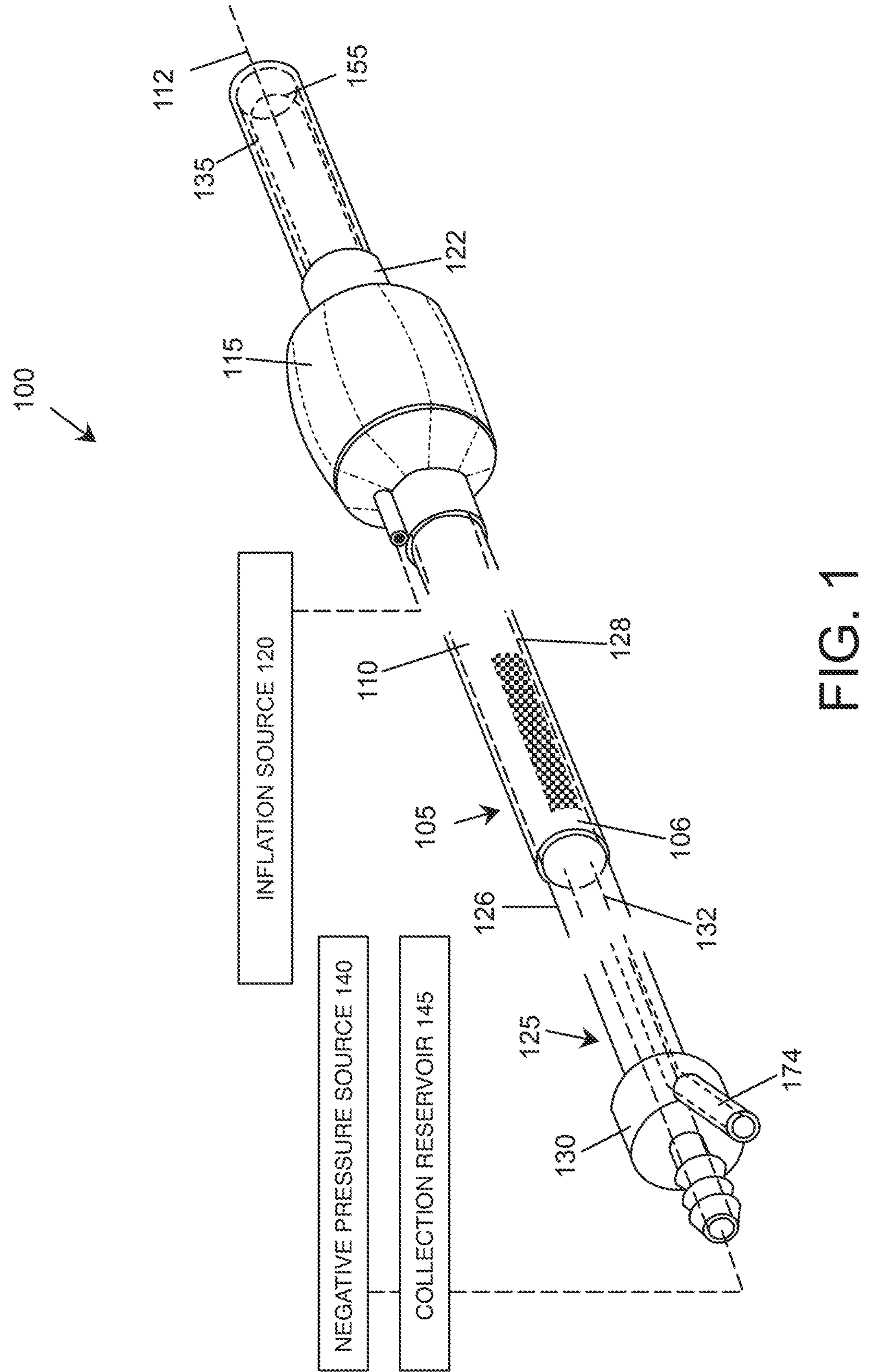
FIG. 1 is a perspective view of a first introducer assembly of a catheter system for treating postpartum hemorrhaging comprising a cervical seal, an introducer sleeve, and an aspiration catheter.

FIG. 1 illustrates a variation of a uterine contraction system 100 that includes an introducer member 105 with a proximal handle portion 106 extending distally as an elongated introducer sleeve 110 extending about longitudinal axis 112 configured for trans-cervical introduction into a patient's uterine cavity. The introducer sleeve 110 carries a cervical scaling component which, in this variation, comprises an inflatable balloon 115 that is adapted for inflation in a patient's birth canal (lower uterus, cervical canal, or vaginal canal) to seal the uterine cavity. The balloon 115 is coupled to an inflation source 120, which typically is a fluid-filled syringe operated by the clinician. The balloon 115 can be fixed to the introducer sleeve 110 or can be carried on a slidable balloon sleeve 122 so that the introducer sleeve 110 can be moved inwardly and outwardly relative to the balloon 115 when expanded and in a fixed location in the patient's cervical canal (see FIG. 5).

Still referring to FIG. 1, the system 100 further includes the highly elongated aspiration catheter 125 with shaft 126 adapted for insertion through an interior passageway 128 in the introducer sleeve 110. The catheter has a proximal handle 130 adapted for gripping and advancing or retracting the catheter 125. The aspiration catheter 125 is further shown in FIGS. 3 and 5 wherein the catheter's elongate shaft 126 has an interior aspiration passageway 132 that communicates with a negative pressure source 140 and collection reservoir 145 (FIG. 1) and filter that together are adapted for (i) collapsing the patient's uterine cavity onto the surface of the catheter working end 135 and into contact with an electrode stimulation catheter described below and for (ii) extracting blood and fluid from the uterine cavity as the uterine walls are collapsed. The collapse of the uterine walls and electrical stimulation described below is intended to cause contraction of the uterine wall muscles, which will further collapse blood vessels and stop hemorrhaging in a postpartum patient.

Figures 3, 4:
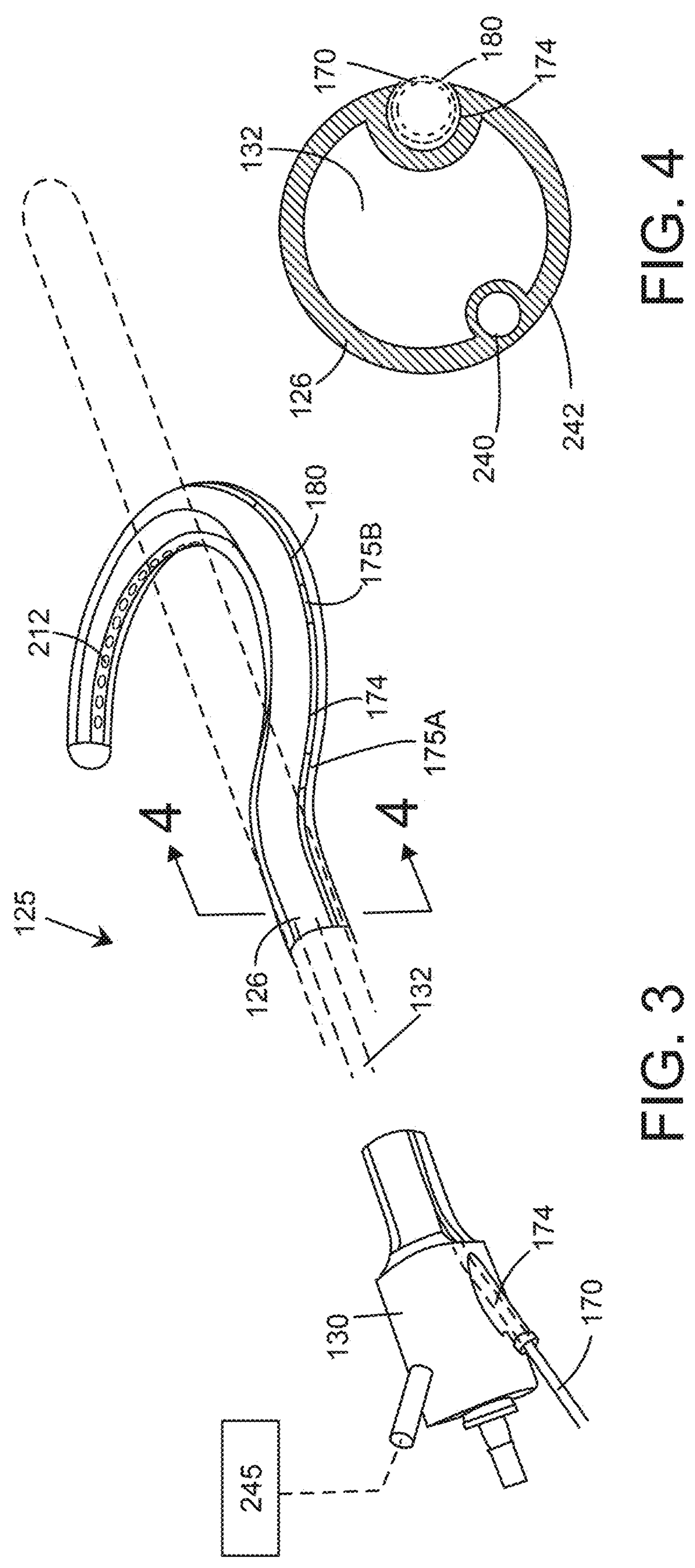
FIG. 3 is a perspective view of the aspiration catheter of FIG. 1 separated from the cervical seal and introducer sleeve.
FIG. 4 is a sectional view of the shaft of the aspiration catheter of FIG. 3.
Figure 5:
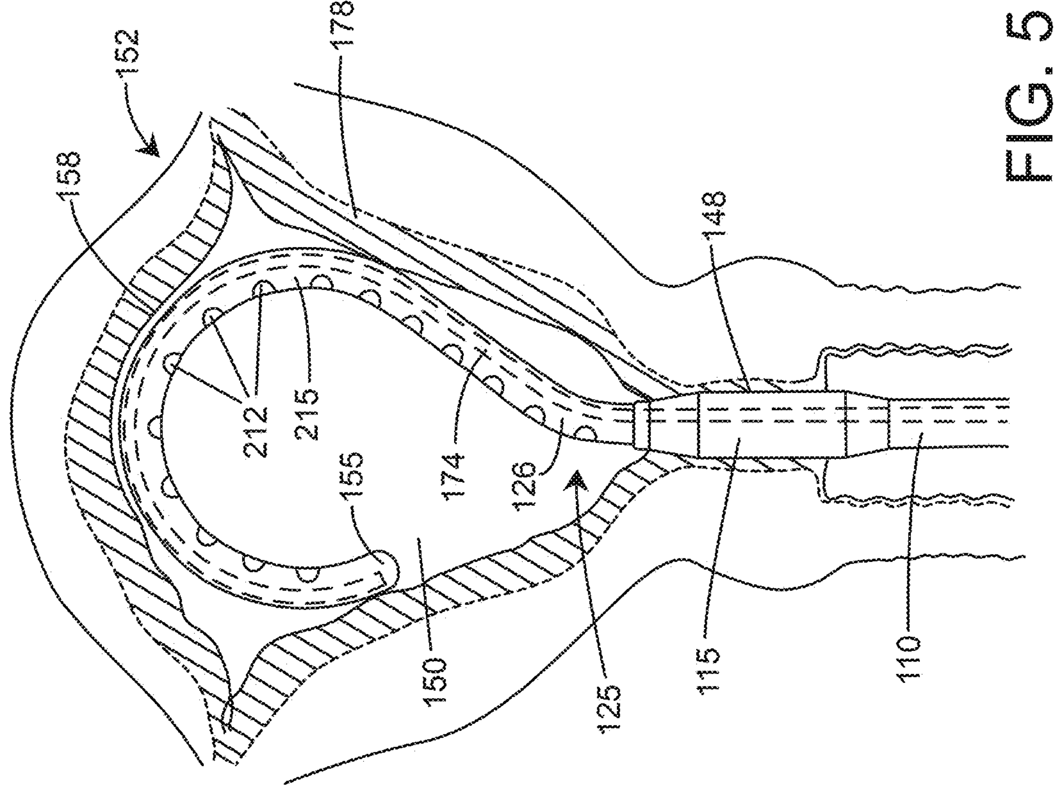
FIG. 5 is a schematic view of the catheter system of FIGS. 1 and 2 in a method of use.
Figure 6:
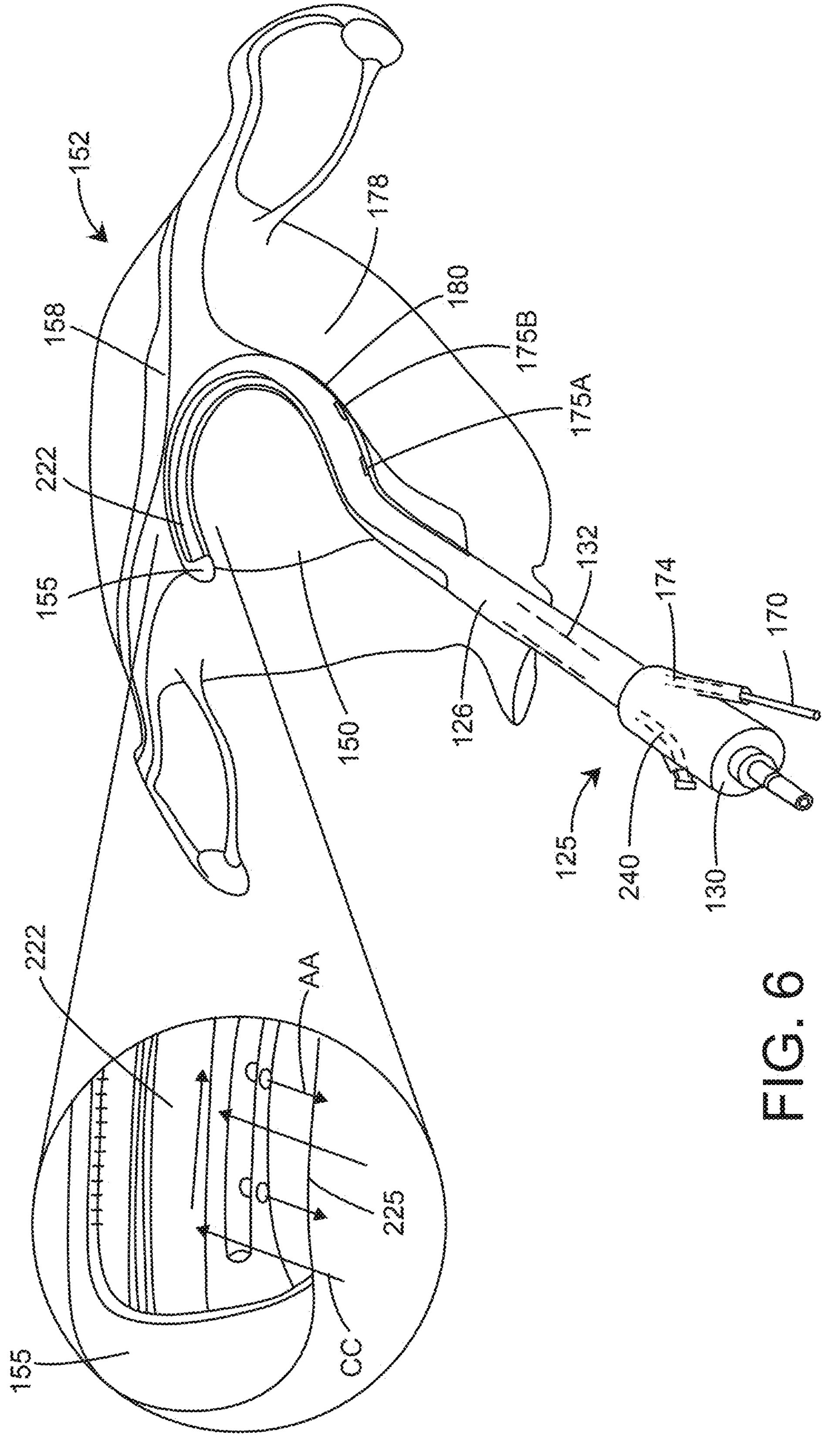
FIG. 6 is a view of the electrical stimulation catheter of FIG. 2 and the aspiration catheter of FIG. 3 in a method not showing the introducer sleeve and cervical seal.

As can be understood from FIGS. 3, 5, and 6, the catheter shaft 126 has working end 135 comprising a flexible material that, when advanced through a cervical canal 148 into a uterine cavity 150 of a uterus 152, the blunt distal tip 155 of the working end 135 will bend and follow the contours of the uterine cavity and the fundus 158 of the uterine cavity (FIG. 5). As can be understood from FIGS. 4 and 5, the working end 135 in the linear shape of FIGS. 1 and 3 are in a tensioned state, and when the working end is in an expanded curved shape as in FIGS. 4 and 5, it moves toward a repose state. FIG. 3A also shows the catheter shaft 126 including a series of ports 212 that are in fluid communication with the interior aspiration passageway 132 to draw negative pressure as discussed herein.

Figure 2:
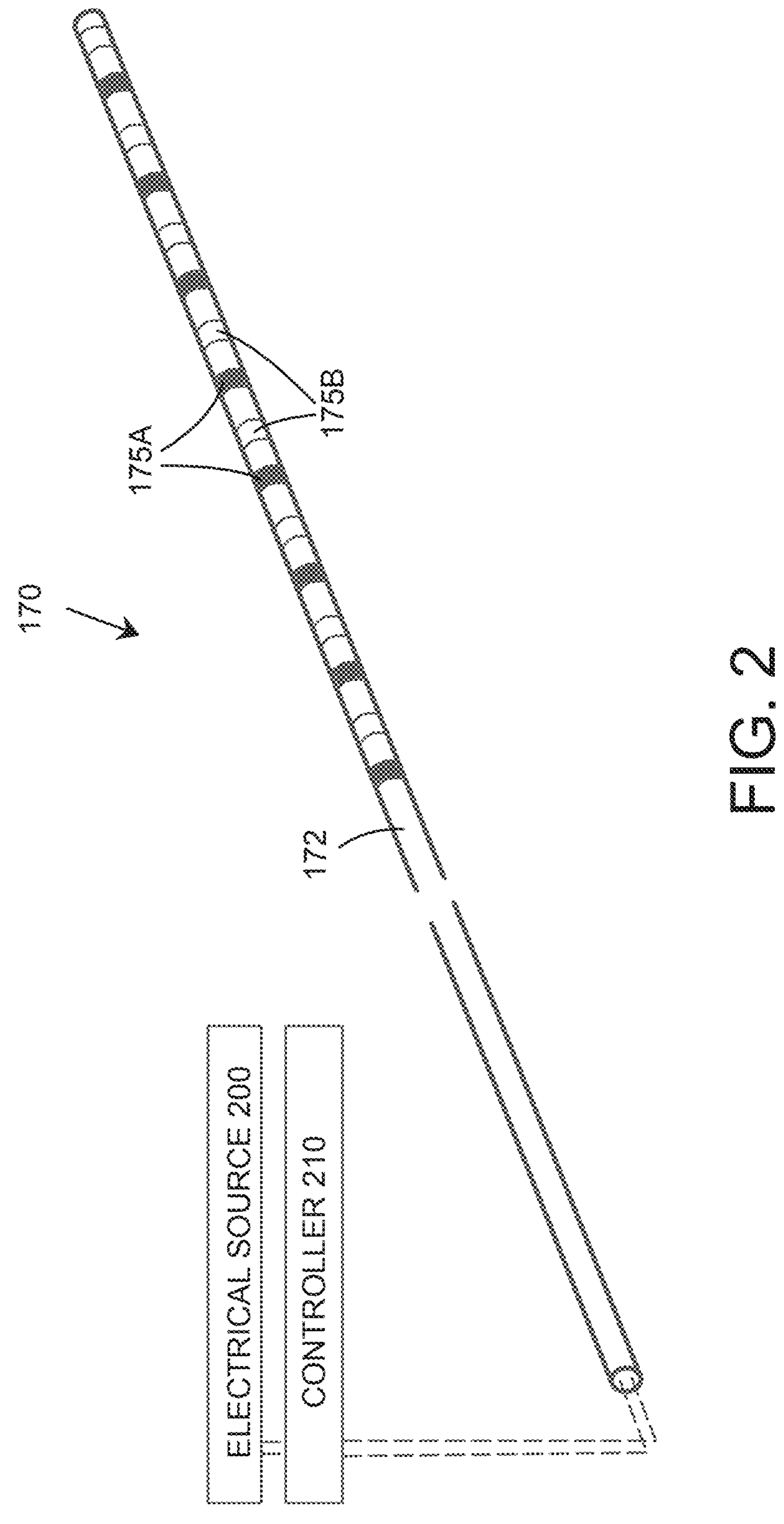
FIG. 2 is a perspective view of a second component of the catheter system for treating postpartum hemorrhaging comprising an electrical stimulation catheter.

FIG. 2 shows the electrical stimulation component of the uterine contraction system 100 that comprises an electrical stimulation catheter 170 that comprises a highly elongated catheter shaft 172 that is adapted for insertion through a passageway 174 in a side of the aspiration catheter 125 (FIGS. 1 and 3-5). As can be seen in FIGS. 2 and 6, the stimulation catheter 170 has a series of opposing polarity electrodes 175A, 175B exposed on a surface of the shaft 172 for delivering electrical current stimulation to a uterine wall 178 (FIGS. 5 and 6). In FIGS. 3 and 4, it can be seen that the passageway 174 in the aspiration catheter 125 is configured with an open edge 180 so that the electrodes 175A, 175B of the stimulation catheter 170 are exposed and will contact the uterine wall 178 in a method of use (FIGS. 5 and 6). In FIG. 2, it can be seen that the stimulation catheter 170 is operatively coupled to an electrical source 200 and a controller 210 for controlling electrical energy delivery to the electrodes 175A and 175B. In this variation, the electrical stimulation catheter 170 is removable from the aspiration catheter 125 and can be reusable. In another system variation, the single-use aspiration catheter can be fitted with the electrode arrangement of FIG. 2 to eliminate the use of a separate stimulation component.

The controller 210 can include a touch screen, a video display, a digital display, and other types of displays to display the stimulation output currents produced by the system for observation by the clinician. In a variation, the controller 210 can be programmed to control various electrical stimulation settings by pre-programmed selected settings or by a clinician using the controls on an interface of the controller 210. In a variation, the electrical source 200 and controller 210 are configured to generate an output current between 0.01 milliamperes and 40.00 milliamperes. The controller 210 can provide pulse widths of electrical current between about 0.1 milliseconds and 1 second. Frequencies of the stimulation current can be adjusted from 0.1 Hertz to 30 Hz or greater. Pulse train durations can be adjusted from 1 second to 1 minute. In addition, output currents can be sinusoidal so as to reduce tissue damage and maximize effect. Additionally, the electrical stimulation current output from the electrical source 200 can be detected by the controller 210, and energy delivery can be automatically terminated if current values are found to be or outside selected prescribed values. In a method of use, the electrical stimulation current can be delivered for at least one minute, at least 5 minutes, or at least 10 minutes.

In FIG. 5, it can be seen in a catheter variation that an interior surface of the aspiration catheter 125 has a plurality of aspiration ports 212 therein for (i) applying the vacuum to the uterine cavity 150 to contract the uterine wall against the working end 135 and electrodes 175A, 175B as well as for (ii) suctioning fluid and blood from the uterine cavity. In this variation, the aspiration ports 212 consist of spaced-apart openings or elongated openings in an inward-facing or medial surface 215 of the catheter shaft. In the variation of FIG. 6, the aspiration port 220 consists of the open side of a U-shaped channel 222 in an inner-facing surface 225 of the catheter shaft 126.

In the variation, the aspiration catheter 125 and the electrical stimulation catheter 170 can be introduced a selected distance through the introducer sleeve 110, so the system 100 is suitable for treating any size uterus.

In the variation shown in FIGS. 3, 4, and 6, an irrigation lumen 240 is provided in a wall 242 of the aspiration catheter 125 (see FIG. 4), wherein the system is adapted to introduce an irrigation fluid from fluid source 245, such as saline into the uterine cavity 150 to assist in lavage or washing blood away from uterine walls 178 and into the aspiration channel 132. In a variation shown in FIG. 6, the inflow of irrigation fluid is indicated at arrows AA, and the fluid outflows into the aspiration channel are indicated at arrows CC. In general, the inflow ports are positioned adjacent to the outflow ports or outflow channel in the wall of the aspiration catheter 125 to wash away blood clots and debris to allow the free flow of blood and fluid from the uterine cavity 150 to the collection reservoir 145.

Figure 7:
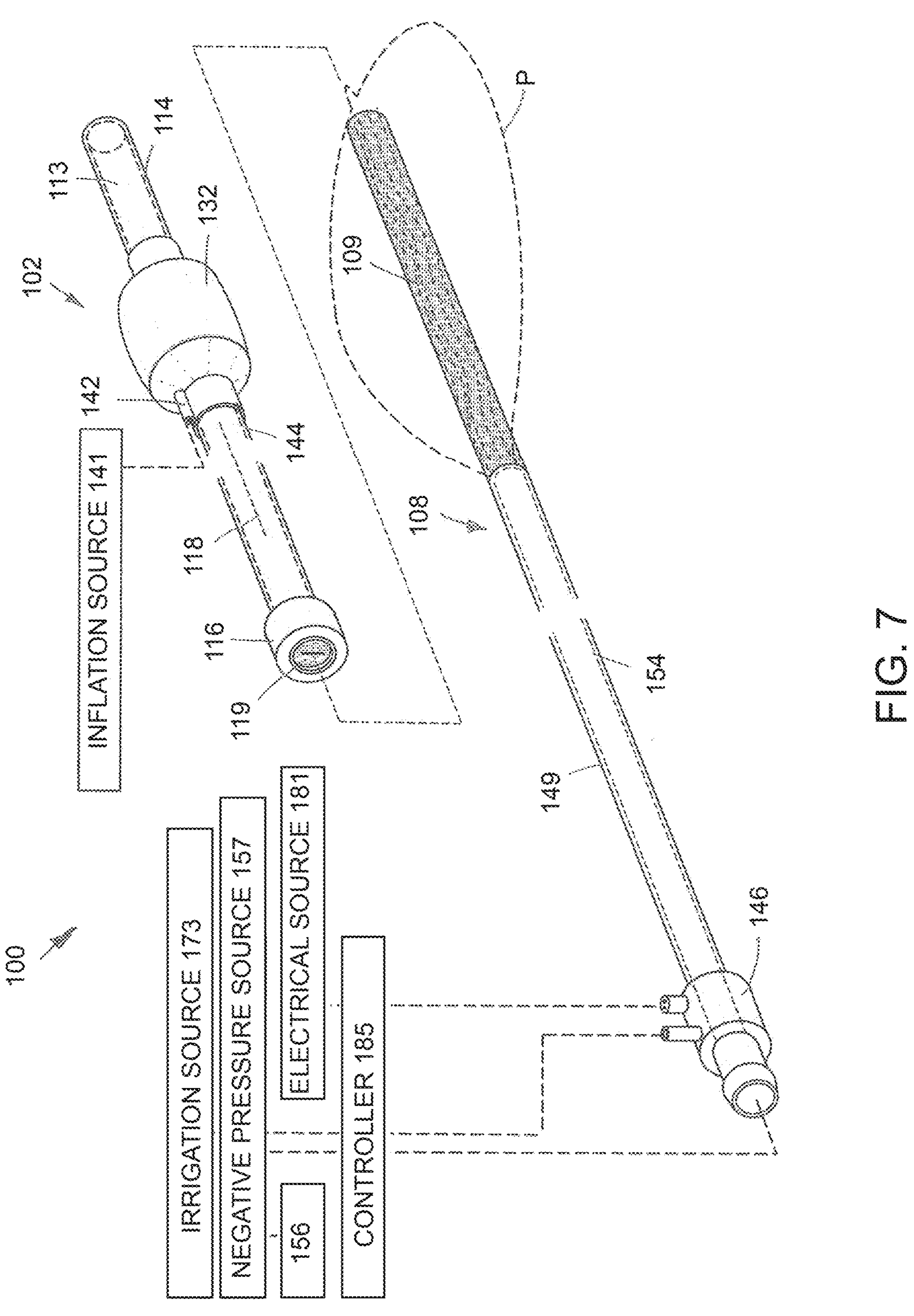
FIG. 7 is a perspective view of another system for treating postpartum hemorrhage comprising an introducer member and a treatment device that uses a negative pressure component and an electrical stimulation component.

FIG. 7 illustrates another variation of a uterine contraction system 100 that includes an introducer member 102 with a treatment device 108 having an expandable working end 109 that is extendable from a lumen 114 in an elongated sleeve 115 of the introducer member 102. FIG. 7 shows the introducer member 102 and treatment device 108 separated from one another. The working end 109 of the treatment device 108 is shown in a pre-deployed, collapsed configuration as if the working end 109 is constrained in the lumen 114 of the sleeve 115. FIG. 7 also shows an expanded periphery P of the working end 109 (dashed line) that illustrates the periphery of an expanded, deployed working end 109 having a planar configuration after outward deployment from lumen 114 of sleeve 115.

Figure 8:
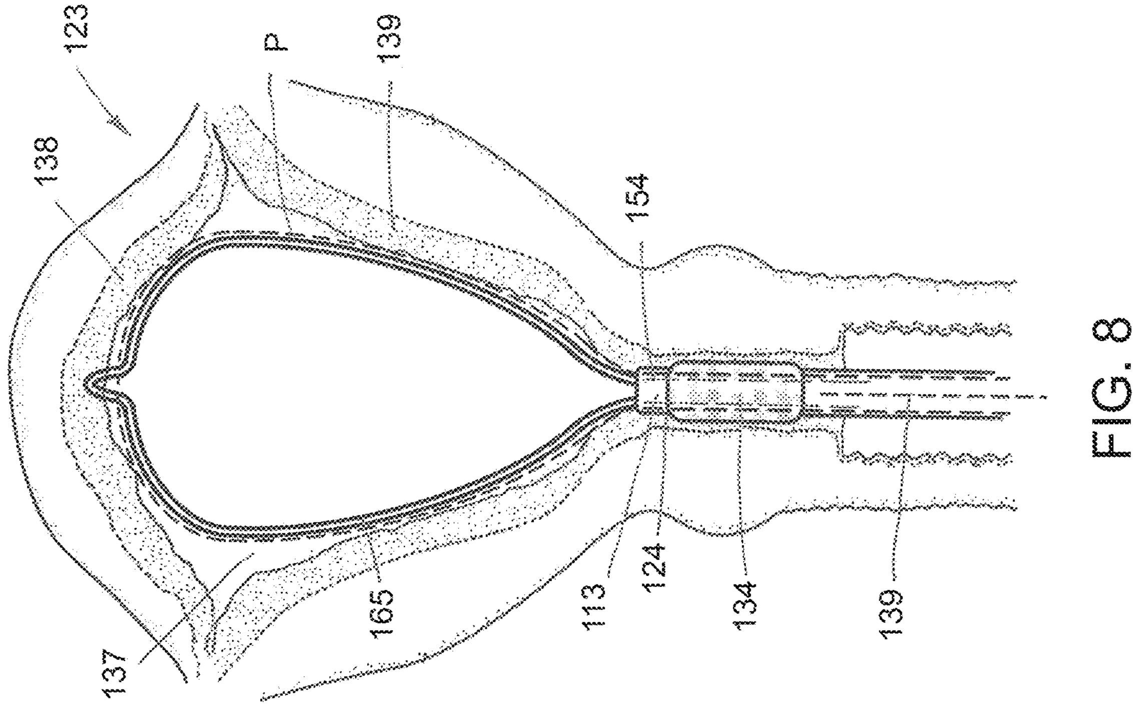
FIG. 8 is a view of an expandable wire frame of the working end of the treatment device of FIG. 7.
Figure 9:
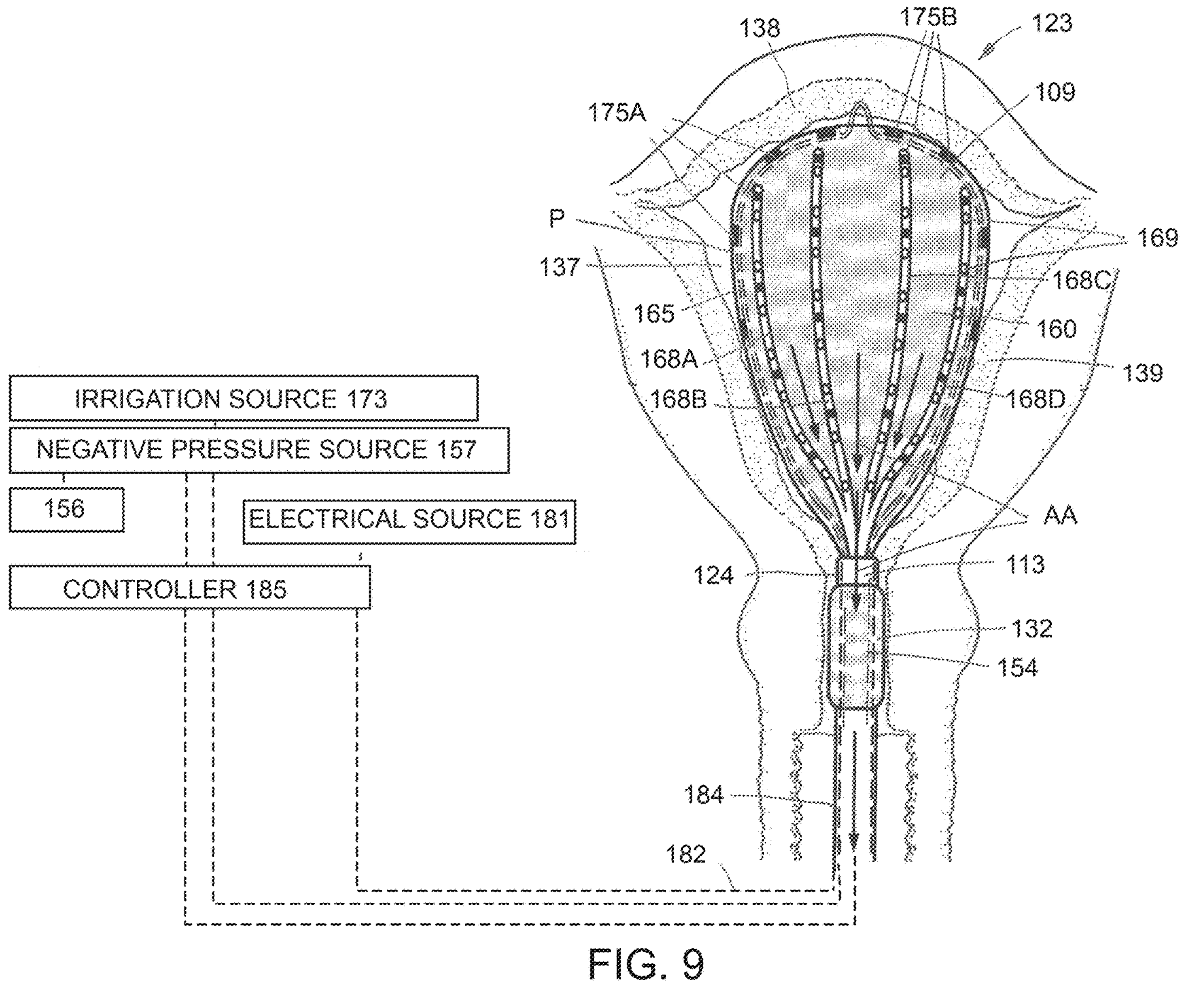
FIG. 9 is a view of the working end of the treatment device of FIGS. 7 and 8 showing the use of the negative pressure source and the electrode arrangement of the electrical stimulation component.
Figure 13:
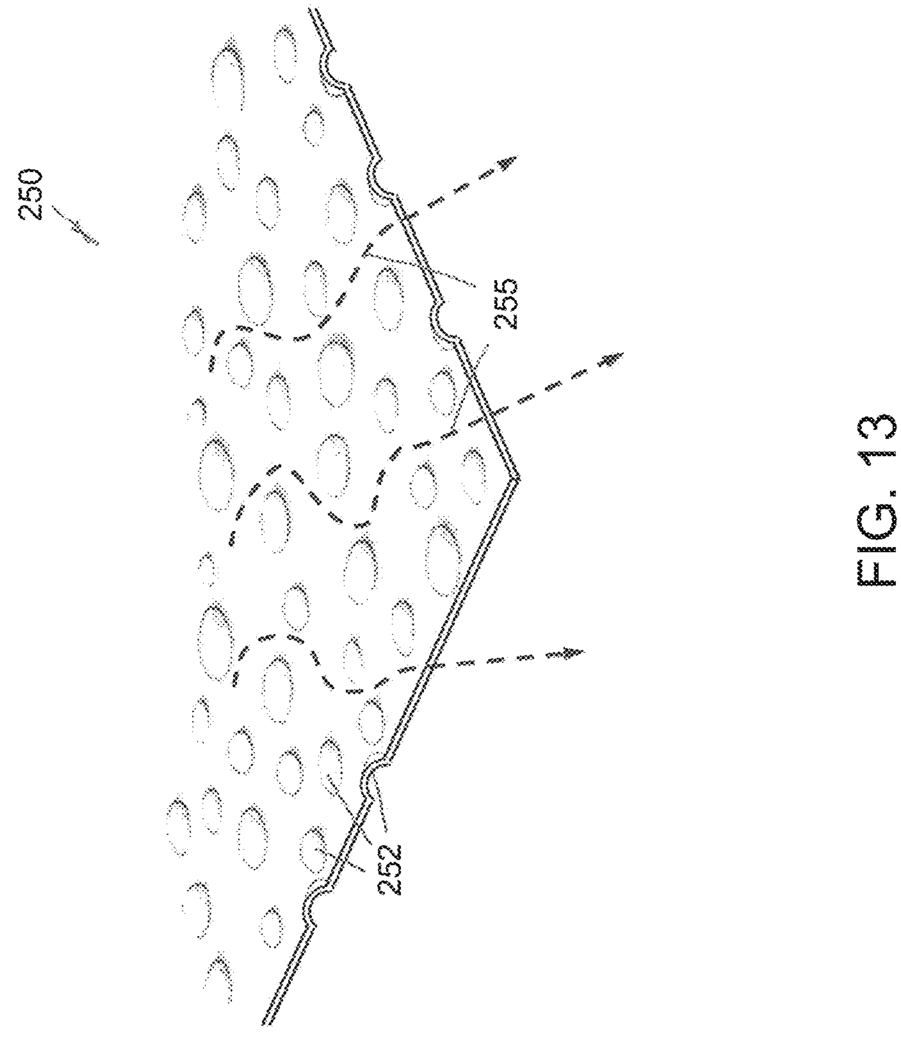
FIG. 13 is an enlarged view of an embossed film of a working end that is similar to the working end of FIG. 9.

In FIG. 7, the introducer member 102 is illustrated with a proximal grip 116 coupled to the elongated thin-wall sleeve 115 extending about longitudinal axis 118 and is configured for trans-cervical introduction into a patient's uterine cavity as shown in FIGS. 8 and 9. The proximal grip 116 carries an elastomeric instrument seal 119 in a proximal end of the lumen 114. FIGS. 8 and 9 illustrate a patient's uterus 123, cervical canal 124, and uterine cavity 137. The uterus has fundus 138 and uterine walls 139. The introducer sleeve 115 of FIG. 13 has a diameter ranging from 15 mm to 25 mm. A typical introducer sleeve 115 carries a cervical sealing component which, in this variation, comprises an inflatable balloon 134 fixed to sleeve 115 that is adapted for inflation in a patient's lower uterus, cervical canal, and/or vaginal canal to seal the uterine cavity 137. The balloon 134 is coupled to an inflation source 141 by a flow channel 142 that can be in the wall 144 of sleeve 115 or can comprise a separate tubing (FIG. 13). The inflation source 141 typically is a fluid-filled syringe operated by the clinician.

Still referring to FIG. 7, the treatment device 108 of the system 100 comprises a proximal housing 146 coupled to an elongated shaft 149 adapted for insertion through the lumen 114 in the introducer sleeve 115. The proximal housing 146 of treatment device 108 is adapted for gripping and advancing or retracting the shaft 149 through the introducer sleeve 115 after the sleeve 115 has been positioned in the patient as shown in FIGS. 8 and 9. The treatment device 108 is shown in FIGS. 7 to 9 wherein the shaft 149 has an interior extraction channel 154 that communicates with a negative pressure source 157 and collection reservoir 156 that together are adapted for (i) collapsing the patient's uterine cavity and (ii) extracting blood and fluid from the uterine cavity as the uterine walls are collapsed. The collapse of uterine walls 139 (FIG. 15) enhances contraction of uterine wall muscles, which will further collapse blood vessels and assist in stopping hemorrhaging in a postpartum patient.

Figure 10:
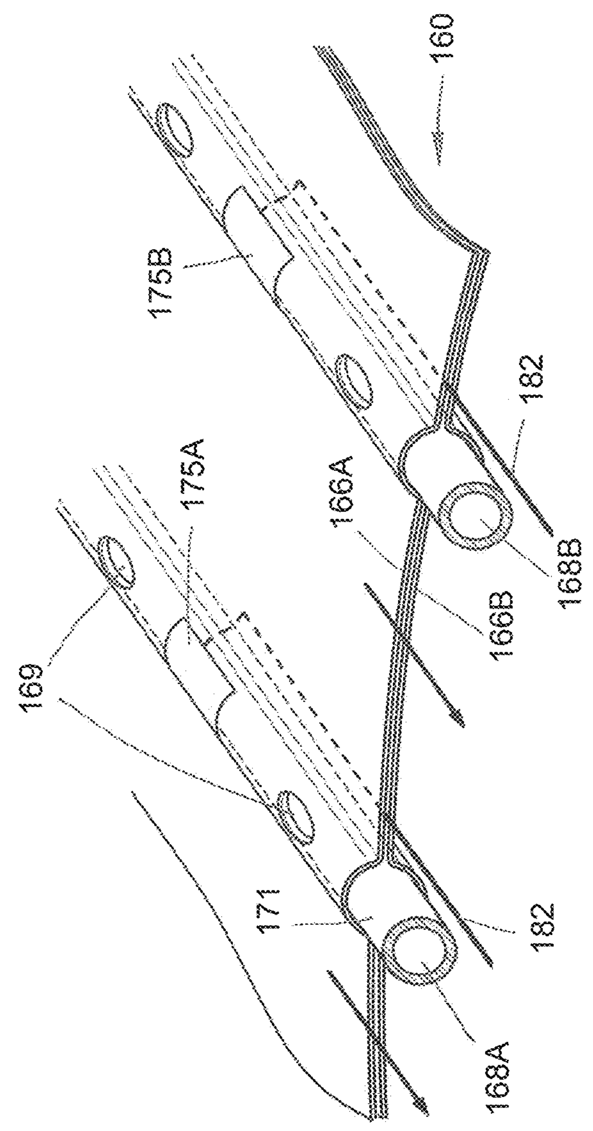
FIG. 10 is an enlarged view of a portion of the working end of FIG. 9.

As can be seen in FIGS. 9 and 10, the working end 109 of treatment device 108 comprises a thin, foldable film 160 and an expandable-collapsible support member or frame 165 (FIG. 14) of a spring material such as NiTi or stainless steel. The support member 165 can have a suitable shape ranging from a round shape to a somewhat triangular shape that will effectively expand to the dimensions of a patient's uterus 123 (see FIG. 14). In a variation, the film 160 comprises a biocompatible polymer and often is two thin films **166*a* and 166*b* that are bonded together as shown in FIG. 10. In a variation, the film 160 carries a plurality of non-collapsible flow channels with four flow channels 168A-168D shown in FIG. 10. As can be seen in FIG. 10, each flow channel has a plurality of ports 169 along the length of each channel. In a variation, the flow channels 168A-168D comprise a lumen within flexible tubing 171 that is sandwiched between and bonded to the two thin films 166*a* and 166*b*. In a method of use described below, the flow channels 168A-168D and ports 169 are used both to provide a fluid flow from an irrigation source 173 into the uterine cavity 137 and thereafter to apply a negative pressure from the negative pressure source 157 to suction the uterine walls against the working end 109 and ports 169**.

FIGS. 7, 9, and 10 further show an electrical stimulation component of the treatment device 108 that comprises a plurality of opposing polarity electrodes 175A, 175B exposed on a surface of the film 160 for delivering electrical current stimulation to uterine walls 139 and fundus 138 (FIG. 9). In FIGS. 7, 9 and 10, it can be seen that the electrodes 175A, 175B are coupled to an electrical source 181 by electrical leads 182 in a wall 184 of shaft 149. A controller 185 is configured for controlling electrical energy from electrical source 181 to the electrodes 175A, 175B. In a variation as shown in FIGS. 9 and 10, the electrodes 175A, 175B are carried in the periphery P of the working end 109 and in the film layers 166*a*, 166*b* overlying the tubing 171 to provide electrode contact with the uterine walls 139 and fundus 138. However, it should be appreciated that the electrodes 175A, 175B can be arranged in any part of both the superior and inferior surfaces of film 160 and the periphery P to apply electrical stimulation current to uterine wall muscles. The density of electrodes may differ around the periphery or surfaces of the working end 109, and in a variation, the electrodes have a denser arrangement in the distal region of the working end 109 as the fundus 138 of the uterus 123 where uterine muscles closer to the fundus play the most significant role in uterine contractions compared to muscles closer to the cervical canal 124.

The controller 185 can include a touch screen, a video display, a digital display, and other types of displays to display the stimulation output currents produced by the system for observation by the clinician. In a variation, the controller 185 can be programmed to control various electrical stimulation settings by pre-programmed selected settings or by a clinician using the controls on an interface of the controller 185. The electrical source 181 can comprise a battery or a wall outlet.

In a variation, the electrical source 181 and controller 185 are configured to generate an output current between 0.01 milliamperes and 40.00 milliamperes. The controller 185 can provide pulse widths of electrical current between about 0.1 milliseconds and about 1 second. Frequencies of the stimulation current can be adjusted from about 0.1 HZ to about 30 Hz or greater. Pulse train durations can be adjusted from about 1 second to 1 minute. In addition, output currents can be sinusoidal so as to reduce tissue damage and maximize effect.

Additionally, the electrical stimulation current output from the electrical source 181 can be detected by the controller 185, and energy delivery can be automatically terminated if current values are found to be outside selected prescribed values. In a method of use, the electrical stimulation current can be delivered for at least one minute, at least 5 minutes, or at least 10 minutes.

In a method of use shown in FIGS. 8 and 9, the sleeve 115 of the introducer member 102 is advanced through the cervical canal 124 to access the uterine cavity 137 of a patient, and thereafter the occlusion balloon 134 is expanded by inflation source 141 in the cervical canal 124. The treatment device 108 is typically carried in the lumen 114 of the introducer 102 as the introducer sleeve 115 is advanced through the cervical canal 124. Alternatively, the treatment device 108 with a collapsed working end 109 can be introduced through seal 119 into the lumen 114 of the introducer member 102 after it is positioned in the patient.

Subsequently, the negative pressure source 157 is activated manually or by the controller 185 to apply negative pressure to the extraction channel 154 of the treatment device 108, wherein such negative pressure then aspirates blood and fluids over the outer inferior and superior surfaces of the working end 109 and into the extraction channel 154. The aspirated blood and fluids are then collected in the collection reservoir 156. During this step, the irrigation source 173 can optionally be activated by the controller 185 or manually to deliver a lavage fluid (e.g., saline) through flow channels 168A-168D to irrigate the surfaces of the working end 109, which assists in the removal of blood and blood clots. The time interval for operating the irrigation source 173 as described above may be from 10 seconds to 2 minutes. It should be appreciated that the negative pressure source 157, when actuated, operates at a sufficiently high setting to collapse the uterine cavity 137. In a variation, the fluid inflows from the irrigation source 173 can be drawn through channels 168A-168D by negative pressure from the negative pressure source 157. In another variation, a positive pressure source may be used to assist the fluid inflow from irrigation source 173 at a low pressure so that the negative pressure is still sufficient to collapse the uterine cavity 137. After the lavage interval, the clinician or controller 185 can operate the negative pressure source to communicate with the flow channels 168A-168D and ports 169 to further suction the uterine walls 138 and fundus 138 against the surfaces of the working end 109. The negative pressure source 157 operates to aspirate blood and fluid from the uterine cavity as indicated by arrows AA.

In the electrical stimulation aspect of the method of use, the clinician activates electrical source 181 to deliver electrical stimulation current to the uterine walls 139 and fundus 138 to cause muscle contraction. In a variation, the electrical source 181 and controller 185 are configured to generate an output current between 0.01 milliamperes and 40.00 milliamperes. A pulse width of electrical current can be selected that ranges from about 0.1 milliseconds to 1 second. The electrical stimulation current can be delivered from 0.1 Hz to 50 Hz. Pulse train durations can be adjusted from 1 second to 1 minute. In a method of use, the electrical current can be delivered to cause muscle stimulation for at least 30 seconds and often one minute to 10 minutes. The typical vacuum pressure during operation of the device is from 50 mm Hg to 90 mm Hg. The treatment device can be left in place in the uterine cavity 137 with negative pressure being applied for at least 10 minutes and often up to 1 hour or up to 3 hours.

Figure 11:
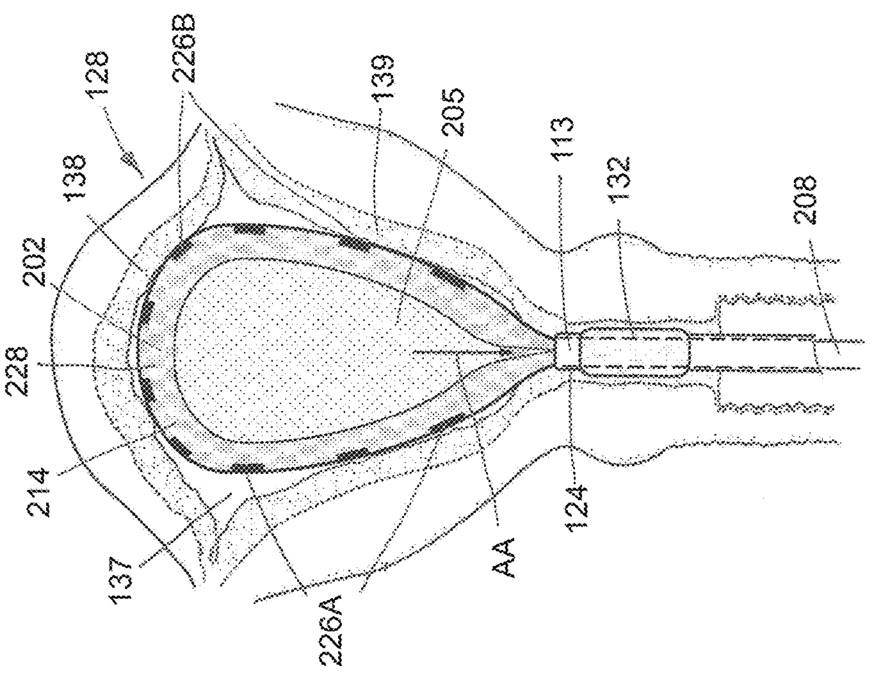
FIG. 11 is a view of another variation of a working end similar to that of FIGS. 9 and 10.

FIG. 11 illustrates another variation of a treatment device 202 that is similar to that of FIGS. 7 and 9, except that the variation of FIG. 11 has a different type of collapsible-expandable working end 205. FIG. 11 illustrates the introducer sleeve 115 and occlusion balloon 134 of FIG. 13 in a patient's cervical canal 124. An elongate shaft 208 of the treatment device 202 extends distally through the introducer sleeve 115 to the deployed, expanded working end 205. In this variation, the working end 205 is configured with an inflatable peripheral support structure 215 comprising an inflation channel coupled to an inflation source (not shown). The inflation source typically comprises a fluid-filled syringe, for example, a saline-filled syringe, that is operated by the clinician. The collapsible working end 205 can be collapsed and carried in a lumen in the shaft 208 and introduced into the uterine cavity 137 through introducer sleeve 115. In the variation of FIG. 11, the plurality of opposing polarity electrodes 226A-226B are carried on an outer surface 228 of the inflatable support structure 214. The negative pressure source 157 operates as described previously to aspirate blood and fluid from the uterine cavity as shown by arrow AA in FIG. 11.

Figure 12:
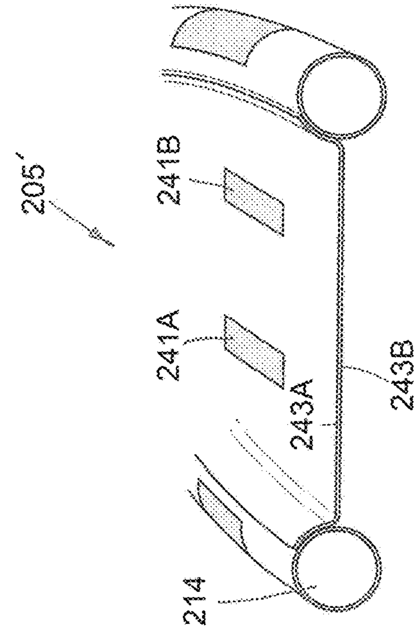
FIG. 12 is a view of another variation of a working end similar to that of FIG. 11.

FIG. 12 is a sectional view of another variation of working end 205' with an inflatable peripheral support structure 214 similar to that of FIG. 11. In this variation, additional opposing polarity electrodes 241A-241B are carried on inferior and superior surfaces 243A, 243B of a central portion 244 of the working end 205'. The negative pressure source 157 again operates as described previously to aspirate blood and fluid from the uterine cavity 137.

FIG. 13 illustrates the construction of another variation of a film material used in a working end of a treatment device, such as the working ends of FIGS. 9-12. In this variation, the collapsible-expandable working end can be expanded by a wire support frame, an inflatable peripheral support structure, an inflatable unrolling or unfolding thin-wall structure, an inflatable everting thin-wall structure, or the like. As described above, the working end can carry channels for lavage and any form of electrode arrangement to provide electrical stimulation. FIG. 13 illustrates a thin film 250 embossed with three-dimensional features 252 that create interconnected flow channels 255 throughout the surface of the film. The flow channels 255 allow for fluid flows over the surface responsive to the negative pressure source 157 and prevent trapped fluid between the film and walls 139 and fundus 138 of a uterine cavity. FIG. 13 illustrates a single-layer film 250, but multi-layer thin-wall structures fall within the scope of the invention as known in the art of vacuum bag devices, for example, as disclosed in U.S. Pat. No. 5,129,813.

In another variation, a working end of a treatment device can comprise a thin-wall structure that is doped with at least one hemostatic agent. In a variation, the surface of a working end is treated with a kaolin, for example, a polyacrylamide-treated kaolin material. Such kaolin treated materials are described in the following articles: https://palomino-lab.utk.edu/publications/Kim % 20 and %20Palomino-2009.pdf and www.sciencedirect.com/science/article/pii/S2211379717300293?via % 3Dihub In another variation, a working end of a treatment device has a pharmaceutical agent, such as Oxytocin, impregnated into the surface of the working end to promote the contraction of uterine walls.

Figure 14:
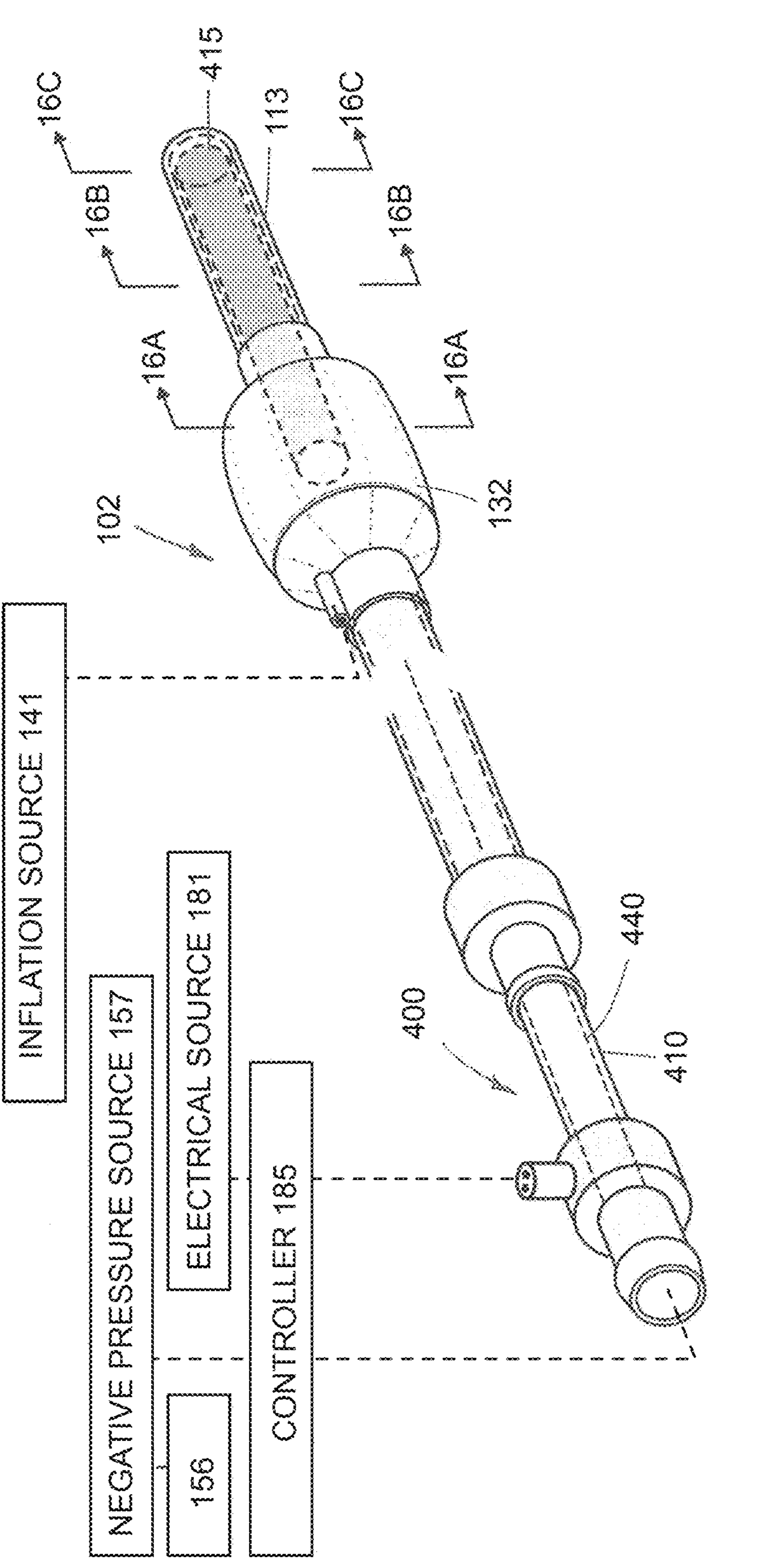
FIG. 14 is a perspective view of another system for treating postpartum hemorrhage with a treatment device that uses a negative pressure component and electrical stimulation electrodes in the first and second resilient members.
Figure 15:
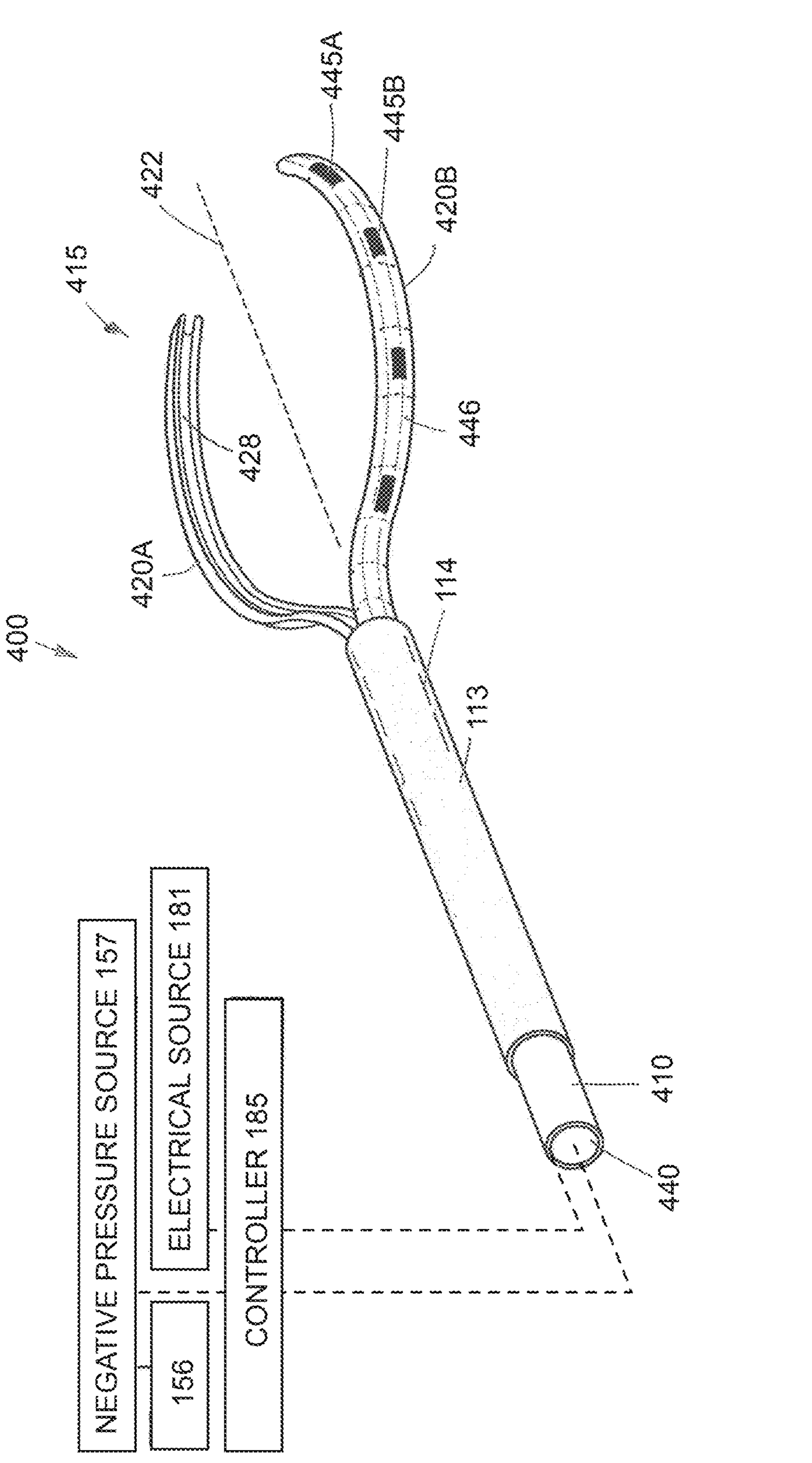
FIG. 15 is a perspective view of the working end of the treatment device of FIG. 14.

FIGS. 14 and 15 illustrate another variation of a treatment device 400, which is used in combination with an introducer member 102 shown in FIG. 14 that is similar to the introducer 102 of FIG. 1 above. The treatment device of FIGS. 14 and 15 again have a shaft 410 extending to a collapsible-expandable working end 415, with the working end collapsed in the lumen 114 of the introducer sleeve 115 in FIG. 14.

Figures 16A, 16B, 16C:
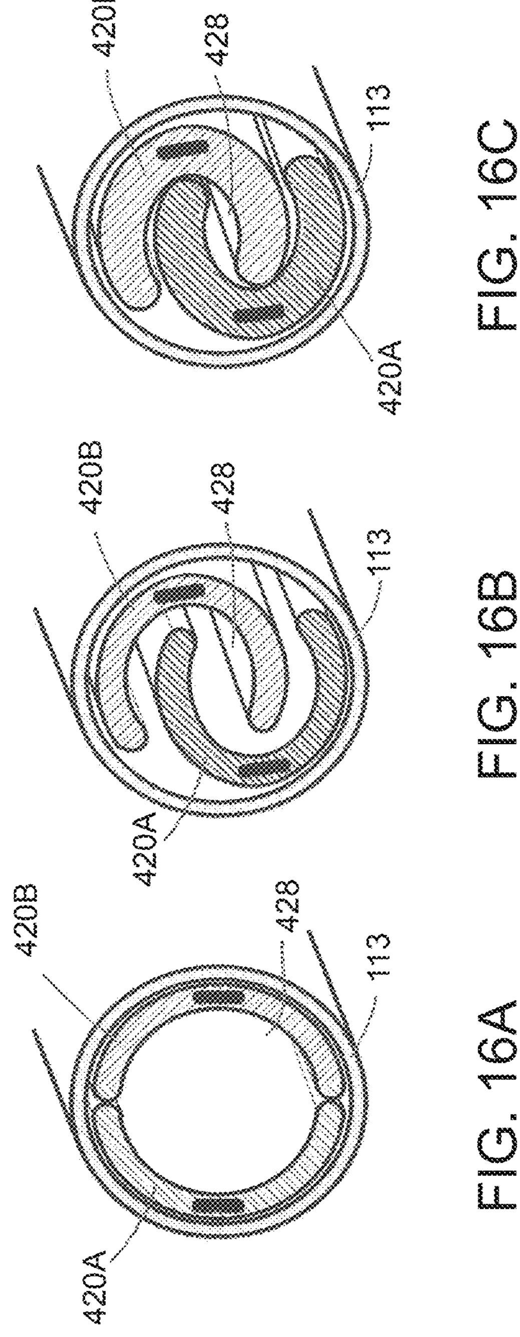
FIG. 16A is a sectional view of a proximal portion of the working end of FIG. 15 collapsed in the constraining sleeve of FIG. 15.
FIG. 16B is a sectional view of a medial portion of the working end of FIG. 15 collapsed in the constraining sleeve.
FIG. 16C is a sectional view of a distal portion of the working end of FIG. 15 collapsed in the constraining sleeve.

FIG. 15 shows the working end 415 after being deployed distally outward from the introducer sleeve 115 where it can be seen that the working end 415 comprises first and second spring-like, flexible support members 420A, 420B that spring open to a rounded shape relative to axis 422 (FIG. 15), where each member will extend substantially around a surface of a uterine cavity. In this variation, the support members 420A, 420B are configured with U-shaped channels 428 (see FIGS. 16A-16C), and the negative pressure source 157 communicates with the channels 428 to suction fluid and blood outwardly and through lumen 440 in the shaft 410 to a collection reservoir. FIGS. 16A-16C show how the flexible support members 420A, 420B collapse and fold into one another when retracted into the lumen 440 of shaft 410 (FIGS. 14 and 15). In this variation, the arrangement of opposing polarity electrodes 445A-445B is carried on an exterior surface 446 of each of the support members 420A, 420B for electrical stimulation of the muscles of the uterine walls and fundus as described above.

In any of the above variations, the introducer member or the treatment device can carry an image sensor and at least one LED for viewing the uterine cavity prior to the application of negative pressure and muscle stimulation.

A number of embodiments have been described. Nevertheless, it will be understood by one of ordinary skill in the art that various modifications may be made without departing from the spirit and scope of the embodiments. Methods recited herein may be carried out in any order of the recited events that is logically possible, as well as the recited order of events. Moreover, additional steps or operations may be provided, or steps or operations may be eliminated to achieve the desired result.

Each of the individual variations or embodiments described and illustrated herein has discrete components and features that may be readily separated from or combined with the features of any of the other variations or embodiments. Modifications may be made to adapt a particular situation, material, composition of matter, process, process act(s), or step(s) to the objective(s), spirit, or scope of the present invention.

All existing subject matter mentioned herein (e.g., publications, patents, and patent applications) is incorporated by reference herein in its entirety. The referenced items are provided solely for their disclosure prior to the filing date of the present application.

This disclosure is not intended to be limited to the scope of the particular forms set forth but is intended to cover alternatives, modifications, and equivalents of the variations or embodiments described herein. Further, the scope of the disclosure fully encompasses other variations or embodiments that may become obvious to those skilled in the art in view of this disclosure.

What is claimed is:

1. A method for treating uterine atony to mitigate postpartum hemorrhaging in a patient, comprising:

positioning an electrode arrangement within a uterine cavity, wherein the electrode arrangement comprises a plurality of electrodes disposed on an outward-facing surface of a working end that is configured to be expandable;

creating a seal near an entrance to the uterine cavity;

applying negative pressure through the working end to contract the uterine cavity and draw a uterine wall into contact with the electrode arrangement; and delivering electrical stimulation current to the uterine wall from the electrode arrangement to cause contraction of uterine muscles and to reduce postpartum bleeding.

2. The method of claim 1, wherein the working end is configured to expand in a planar configuration.

3. The method of claim 1, wherein positioning the electrode arrangement includes introducing the working end into the uterine cavity through a birth canal of the patient.

4. The method of claim 1, wherein positioning the electrode arrangement includes the working end expanding from a linear contracted shape for introduction to an expanded planar shape.

5. The method of claim 4, wherein the linear contracted shape is a tensioned state of the working end and the expanded planar shape is a repose state of the working end.

6. The method of claim 1, further including introducing a lavage fluid from the working end into the uterine cavity.

7. The method of claim 1, further including extracting at least one of blood and irrigation fluid from the uterine cavity with the negative pressure.

8. The method of claim 1, wherein delivering electrical stimulation current comprises maintaining electrical stimulation current for at least 1 minute, at least 5 minutes or at least 10 minutes.

9. The method of claim 1, wherein applying negative pressure comprises maintaining negative pressure for at least 10 minutes.

10. The method of claim 1, wherein the electrical stimulation current is delivered by an electrical source and controller that generates an output current between 0.01 milliamperes and 40.00 milliamperes.

11. The method of claim 10, wherein the electrical source comprises a battery.

12. The method of claim 1, wherein the electrical stimulation current is delivered with pulse width that ranges from about 0.1 millisecond to 1 second.

13. The method of claim 1, wherein the electrical stimulation current has pulse train durations from 1 second to 1 minute.

14. The method of claim 1, wherein the electrical stimulation current is delivered from 0.1 Hz to 50 Hz.

15. The method of claim 1, wherein the negative pressure is from 50 mm Hg to 90 mm Hg.

16. A system for treating postpartum hemorrhaging in a patient, comprising:

a device configured for trans-cervical introduction into a uterine cavity of a patient comprising an elongated shaft with an expandable working end;

a negative pressure source coupled to an extraction lumen in the elongated shaft;

an electrode arrangement carried by the expandable working end; and an electrical source and controller coupled to the electrode arrangement adapted to deliver electrical stimulation to walls of the uterine cavity.

17. The system of claim 16, further comprising an expandable seal carried on the elongated shaft.

18. The system of claim 17, wherein the expandable seal comprises a balloon.

19. The system of claim 16, wherein the expandable working end is expanded by at least one resilient metal member.

20. The system of claim 16, wherein the electrode arrangement is disposed on a peripheral surface of the expandable working end.

21. The system of claim 16, wherein the electrode arrangement is disposed on an inferior surface and a superior surface of the expandable working end.

* * * * *